(12) United States Patent
Umekawa et al.

(10) Patent No.: US 10,492,732 B2
(45) Date of Patent: Dec. 3, 2019

(54) LIVING-BODY INFORMATION MEASUREMENT DEVICE AND NON-TRANSITORY COMPUTER READABLE MEDIUM

(71) Applicant: FUJI XEROX CO., LTD., Tokyo (JP)

(72) Inventors: Hideyuki Umekawa, Kanagawa (JP); Kazuhiro Sakai, Kanagawa (JP); Manabu Akamatsu, Kanagawa (JP); Tomoaki Kojima, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 305 days.

(21) Appl. No.: 15/229,192

(22) Filed: Aug. 5, 2016

(65) Prior Publication Data

US 2017/0273636 A1 Sep. 28, 2017

(30) Foreign Application Priority Data

Mar. 28, 2016 (JP) ................................. 2016-064454
Mar. 28, 2016 (JP) ................................. 2016-064455
Mar. 28, 2016 (JP) ................................. 2016-064456

(51) Int. Cl.
*A61B 5/00* (2006.01)
*A61B 5/026* (2006.01)
(Continued)

(52) U.S. Cl.
CPC .......... *A61B 5/7278* (2013.01); *A61B 5/0261* (2013.01); *A61B 5/14551* (2013.01);
(Continued)

(58) Field of Classification Search
CPC ... A61B 5/7278; A61B 5/725; A61B 5/14551; A61B 5/0261; A61B 5/7275;
(Continued)

(56) References Cited

U.S. PATENT DOCUMENTS 4,167,331 A * 9/1979 Nielsen .............. A61B 5/14551
356/39
2010/0056887 A1 3/2010 Kimura et al.
(Continued)

FOREIGN PATENT DOCUMENTS

JP 7-265284 A 10/1995
JP 4475601 B2 6/2010

OTHER PUBLICATIONS

Communication dated Jul. 22, 2019 by the State Intellectual Property Office of the P.R. of China in application No. 201610806366.7.

*Primary Examiner* — Eric F Winakur
*Assistant Examiner* — Abid A Mustansir
(74) *Attorney, Agent, or Firm* — Sughrue Mion, PLLC

(57) ABSTRACT

Provided is a living-body information measurement device including a first light emitting element and a second light emitting element each that emits different light in wavelength, a light receiving element that receives the light emitted from the first light emitting element and the second light emitting element, a control unit that controls a continuous light-emission period of each of the first light emitting element and the second light emitting element so that the continuous light-emission period of the second light emitting element is shorter than the continuous light-emission period of the first light emitting element, and a measuring unit that measures plural living-body information based on the light received in the light receiving element.

14 Claims, 10 Drawing Sheets

(51) Int. Cl.
*A61B 5/1455* (2006.01)
*A61B 5/0295* (2006.01)

(52) U.S. Cl.
CPC ............ *A61B 5/725* (2013.01); *A61B 5/0295* (2013.01); *A61B 5/14552* (2013.01); *A61B 5/7203* (2013.01); *A61B 5/7225* (2013.01); *A61B 5/7257* (2013.01); *A61B 5/7275* (2013.01); *A61B 2562/0238* (2013.01)

(58) Field of Classification Search
CPC .......... A61B 2562/0238; A61B 5/7203; A61B 5/14552; A61B 5/0295; A61B 5/7225; A61B 5/7257
See application file for complete search history.

(56) References Cited

U.S. PATENT DOCUMENTS

| | | | |
|---|---|---|---|
| 2011/0112387 A1* | 5/2011 | Li | A61B 5/14551 600/324 |
| 2013/0296668 A1* | 11/2013 | Kalathil | A61B 5/14551 600/323 |
| 2017/0251936 A1* | 9/2017 | Sawado | A61B 5/02007 |

* cited by examiner

LIVING-BODY INFORMATION MEASUREMENT DEVICE AND NON-TRANSITORY COMPUTER READABLE MEDIUM

CROSS-REFERENCE TO RELATED APPLICATIONS

This application is based on and claims priority under 35 USC 119 from Japanese Patent Application Nos. 2016-064454 filed Mar. 28, 2016, 2016-064455 filed Mar. 28, 2016, and 2016-064456 filed Mar. 28, 2016.

BACKGROUND

Technical Field

The present disclosure relates to a living-body information measurement device and a non-transitory computer readable medium.

SUMMARY

According to an aspect of the invention, there is provided a living-body information measurement device including:

a first light emitting element and a second light emitting element each that emits different light in wavelength;

a light receiving element that receives the light emitted from the first light emitting element and the second light emitting element;

a control unit that controls a continuous light-emission period of each of the first light emitting element and the second light emitting element so that the continuous light-emission period of the second light emitting element is shorter than the continuous light-emission period of the first light emitting element; and a measuring unit that measures plural living-body information based on the light received in the light receiving element.

BRIEF DESCRIPTION OF THE DRAWINGS

Exemplary embodiments of the present disclosure will be described in detail based on the following figures, wherein.

DETAILED DESCRIPTION

Figure 1:
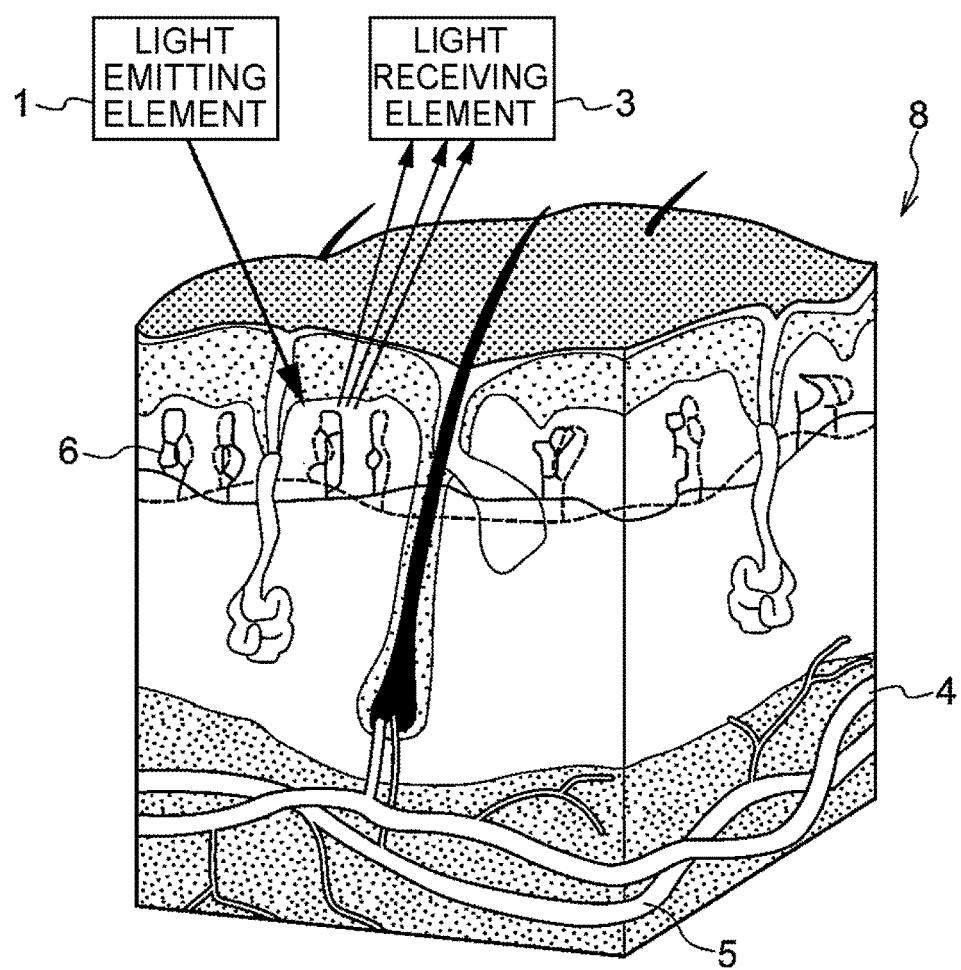
FIG. 1 is a schematic diagram illustrating a measurement example of blood flow information and an oxygen saturation in the blood.

Hereinafter, exemplary embodiments of the present disclosure will be described in detail with reference to the accompanying drawings. Throughout the drawings, the same elements, operations or functions are denoted by the same reference numerals or symbols and explanation thereof will not be repeated for the purpose of brevity.

First, referring to FIG. 1, a method of measuring a blood flow information and an oxygen saturation in the blood, as one example of living-body information on the blood among living-body information, will be described with reference to FIG. 1.

As illustrated in FIG. 1, when light is emitted from a light emitting element 1 to penetrate through the body of a patient (a living body 8) and is received in a light receiving element 3, blood flow information and an oxygen saturation in the blood are measured by using the intensity of light reflected by or transmitted through arteries 4, veins 5 and capillaries 6 spread throughout the living body 8, i.e., measured using the amount of reflected or transmitted light received in the light receiving element 3.

(Measurement of Blood Flow Information)

Figure 2:
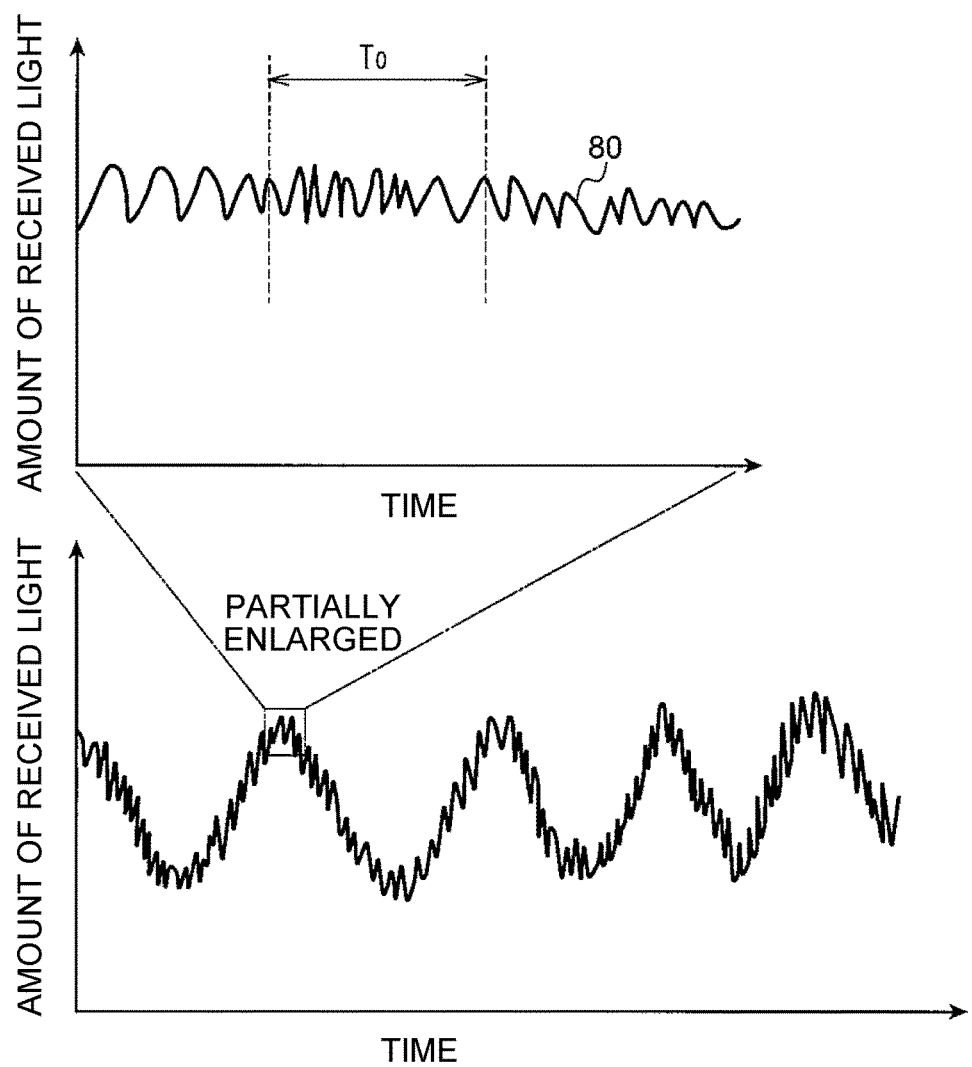
FIG. 2 is a graph illustrating one example of a change in an amount of received light due to reflected light from a living body.

FIG. 2 is one example of a curve 80 that represents the amount of reflected light received by the light receiving element 3. In the graph of FIG. 2, the horizontal axis represents time and the vertical axis represents an output of the light receiving element 3, i.e., the amount of light received by the light receiving element 3.

As illustrated in FIG. 2, the amount of light received in the light receiving element 3 is changed with time. This phenomenon maybe attributed to three optical phenomenons appearing when the living body 8 including the blood vessels is irradiated with light.

The first optical phenomenon is a change in absorption of light due to a change in volume of blood existing in a blood vessel under measurement by pulsation. The blood contains blood cells such as red blood cells and moves through the blood vessels such as capillaries 6. Therefore, the number of blood cells moving through the blood vessels may be changed with the change in the volume of the blood, which may have an influence on the amount of light received in the light receiving element 3.

As the second optical phenomenon, an influence by a Doppler shift may be considered.

Figure 3:
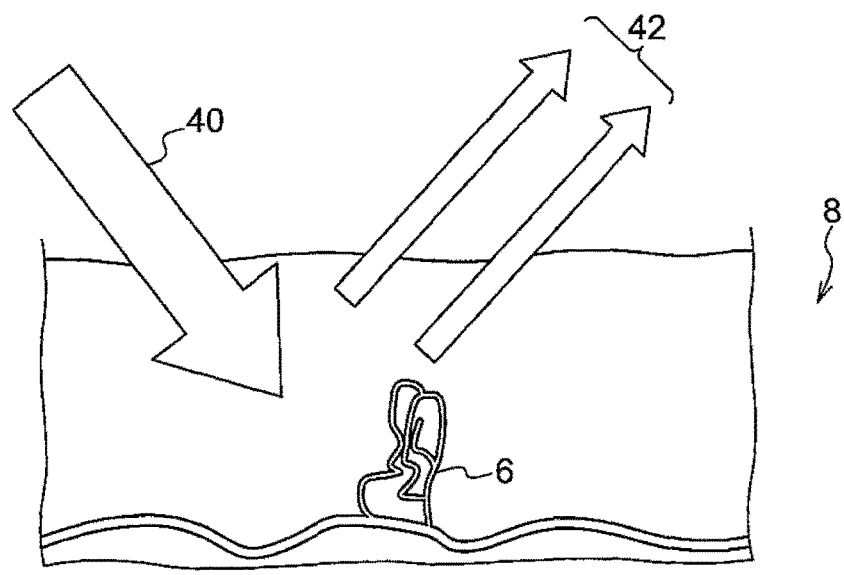
FIG. 3 is a schematic diagram used to explain a Doppler shift which occurs when a blood vessel is irradiated with a laser beam.

As illustrated in FIG. 3, for example, when a region including the capillaries 6 as one example of the blood vessels is irradiated with a coherent light 40 of a frequency $\omega_0$ such as a laser beam from the light emitting element 1, a scattered light 42 scattered by the blood cells moving through the capillaries 6 causes a Doppler shift having a frequency difference $\Delta\omega_0$ determined by a moving speed of the blood cells. In the meantime, the scattered light 42 scattered by the tissues (stationary tissues) such as the skins which do not contain moving bodies such as blood cells maintains the same frequency $\omega_0$ as the irradiated laser beam. Therefore, the frequency $\omega_0+\Delta\omega_0$ of the laser beam scattered by the blood vessels such as the capillaries 6 interferes with the frequency $\omega_0$ of the laser beam scattered by the stationary tissues. Due to such interference, a beat signal having the frequency difference $\Delta\omega_0$ is generated and observed in the light receiving element 3, and as a result, the amount of light received in the light receiving element 3 is changed with time. The frequency difference $\Delta\omega_0$ of the beat signal observed in the light receiving element 3 falls within a frequency range having the upper limit of about several tens kHz, although the frequency difference $\Delta\omega_0$ depends on the moving speed of the blood cells.

The third optical phenomenon may be an influence by speckles.

Figure 4:
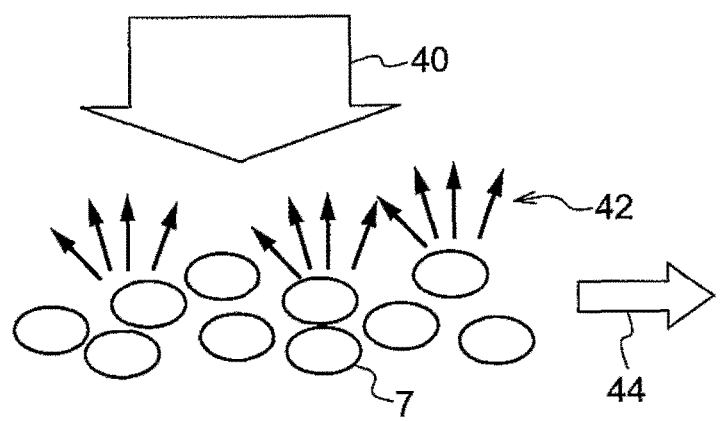
FIG. 4 is a schematic diagram used to explain speckles which occur when a blood vessel is irradiated with a laser beam.

As illustrated in FIG. 4, when the blood cells 7 such as the red blood cells moving through a blood vessel in a direction indicated by an arrow 44 are irradiated with coherent light 40 such as a laser beam from the light emitting element 1, the laser beam striking on the blood cells 7 is scattered in different directions. The scattered beams have different phases and accordingly interfere with one another in a random manner. This results in a light intensity distribution having a random spotted patterns. The light intensity distribution pattern formed in this way is called a "speckle pattern."

As described above, since the blood cells 7 move through the blood vessel, a state of light scattering in the blood cells 7 is changed and accordingly the speckle pattern is changed with time. As a result, the amount of light received in the light receiving element 3 is changed with time.

Figure 5:
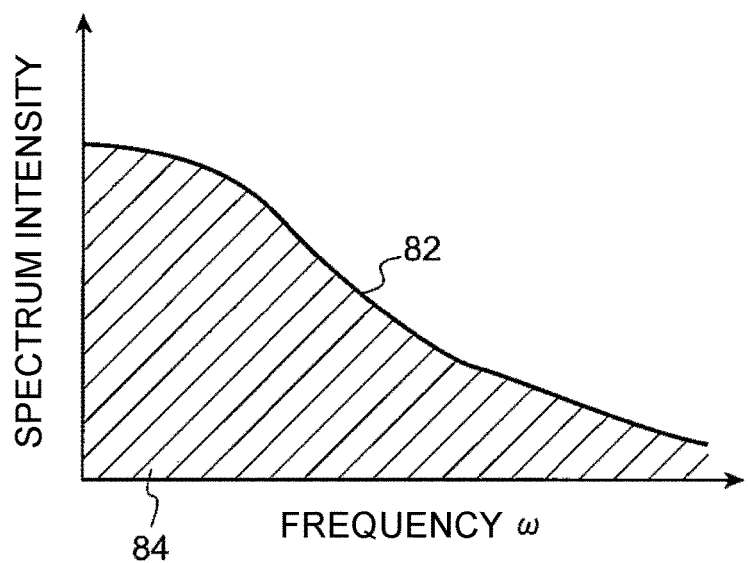
FIG. 5 is a graph illustrating one example of a spectrum distribution with respect to a change in an amount of received light.

Next, one example of a method of obtaining information on a blood flow will be described. When the amount of received light of the light receiving element 3 changed with time is obtained as illustrated in FIG. 2, the data included in a range of unit time $T_0$ are extracted and then subjected to, for example, the fast Fourier transform (FFT), thereby obtaining a spectrum distribution for each frequency $\omega$. FIG. 5 is a graph showing a curve 82 representing an example of the spectrum distribution for each frequency $\omega$ in the unit time $T_0$. In the graph of FIG. 5, the horizontal axis represents a frequency $\omega$ and the vertical axis represents a spectrum intensity.

Here, the blood volume is proportional to a value obtained by normalizing the area of power spectrum, which is indicated by a hatched region 84 surrounded by the horizontal axis and the vertical axis of the curve 82, with the total light amount. In addition, since a blood velocity is proportional to a frequency average of the power spectrum represented by the curve 82, the blood velocity is proportional to a value obtained by dividing a value, which is obtained by integrating a product of the frequency w and the power spectrum at the frequency $\omega$ with respect to the frequency $\omega$, by the area of the hatched region 84.

In addition, since the blood flow is represented by a product of the blood volume and the blood velocity, the blood flow may be obtained from a calculation formula of the blood volume and the blood velocity. The blood flow, the blood velocity and the blood volume are one example of the blood flow information without being limited thereto.

Figure 6:
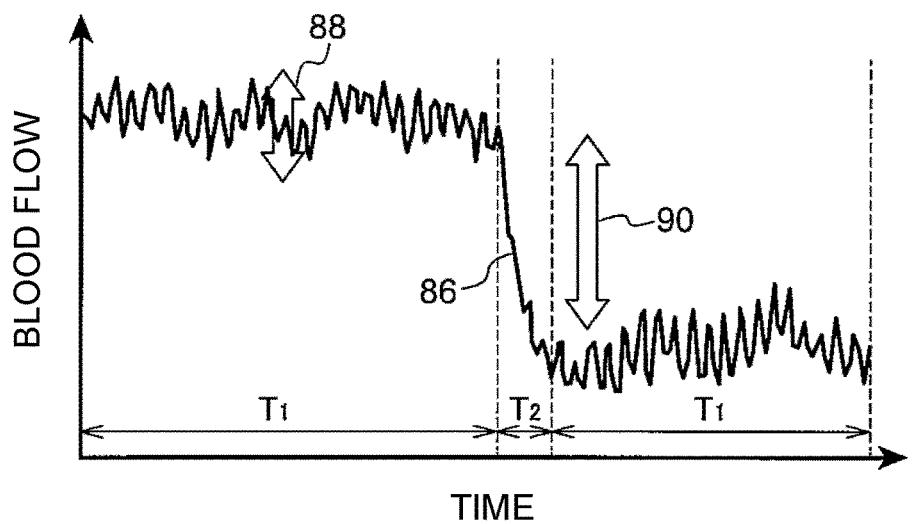
FIG. 6 is a graph illustrating one example of a change in blood flow.

FIG. 6 is a graph showing a curve 86 representing an example of the calculated change in the blood flow per unit time $T_0$. In the graph of FIG. 6, the horizontal axis represents a time and the vertical axis represents a blood flow.

As illustrated in FIG. 6, while the blood flow varies with time, the trend of variation may be classified into two types. For example, in FIG. 6, a variation range 90 of the blood flow in an interval $T_2$ is larger than a variation range 88 of the blood flow in an interval $T_1$. This may be because the change of the blood flow in the interval $T_1$ is mainly due to the motion of a pulse, whereas the change of the flood flow in the interval $T_2$ is due to, for example, the congestion or the like.

(Measurement of Oxygen Saturation)

Next, measurement of an oxygen saturation in the blood will be described. The oxygen saturation in the blood is an indicator that indicates a degree of hemoglobin bonded to oxygen in blood. As the oxygen saturation is reduced in the blood, a symptom such as anemia or the like is apt to occur.

Figure 7:
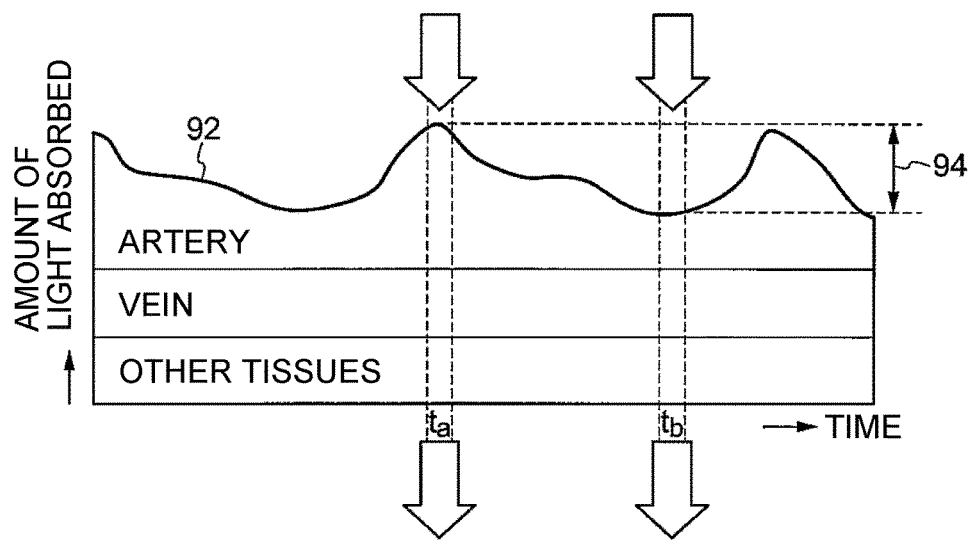
FIG. 7 is a graph illustrating one example of a change in absorbance of light absorbed in a living body.

FIG. 7 is a conceptual graph illustrating the change in absorbance of light absorbed in, for example, the living body 8. As illustrated in FIG. 7, amount of light absorbed in the living body 8 shows a tendency of variation with time.

In addition, referring to the contents of the variation of amount of light absorbed in the living body 8, it is known that the amount of light absorbed is mainly varied by the arteries 4 but may be negligible in other tissues including the veins 5 and the stationary tissues as compared to the arteries 4. This is because the arterial blood pumped from the heart moves through the blood vessels with a pulse wave and the arteries 4 expand/contract along the sectional direction of the arteries 4 with time, thereby causing a change in thickness of the arteries 4. In FIG. 7, the range indicated by an arrow 94 represents a variation of amount of light absorbed corresponding to the change in thickness of the arteries 4.

In FIG. 7, assuming that the amount of received light at time $t_a$ is $I_a$ and the amount of received light at time $t_b$ is $I_b$, a variation $\Delta A$ of amount of light absorbed due to the change in thickness of the arteries 4 is expressed by the following equation (1)

$$\Delta A = \ln(I_b/I_a) \qquad (1)$$

In the meantime, it is known that the hemoglobin bonded to the oxygen flowing through the arteries 4 (oxidized hemoglobin) is apt to absorb light of an infrared (IR) region having a wavelength of about 880 nm or so and the hemoglobin not bonded to the oxygen (reduced hemoglobin) is apt to absorb light of a red region having a wavelength of about 665 nm or so. Further, it is known that the oxygen saturation has a proportional relationship with a ratio of the variation $\Delta A$ of amount of light absorbed at different wavelengths.

Accordingly, in comparison with other combinations of wavelengths, by using the infrared light (IR light) and the red light, which are likely to produce a difference in amount of light absorbed between the oxidized hemoglobin and the reduced hemoglobin, to calculate a ratio of variation $\Delta A_{IR}$ of amount of light absorbed when the living body 8 is irradiated with the IR light to variation $\Delta A_{Red}$ of amount of light absorbed when the living body 8 is irradiated with the red light, the oxygen saturation S is calculated according to the following equation (2). In the equation (2), k is a proportional constant.

$$S=k(\Delta A_{Red}/\Delta A_{IR}) \quad (2)$$

That is, when the oxygen saturation in the blood is calculated, plural light emitting elements 1 emitting light having different wavelengths, specifically, a light emitting element 1 emitting IR light and a light emitting element 1 emitting red light, are caused to emit light in such a manner that their light-emission periods preferably do not overlap with each other, although the light-emission periods may partially overlap with each other. Then, the reflected light or transmitted light by each light emitting element 1 is received in the light receiving element 3 and the oxygen saturation in the blood is measured by calculating the equations (1) and (2) or known equations obtained by modifying these equations (1) and (2) from the amount of received light at respective light receiving points.

As a known equation obtained by modifying the equation (1), the variation $\Delta A$ of amount of light absorbed may be expressed as the following equation (3) by transforming the equation (1).

$$\Delta A = \ln I_b - \ln I_a \quad (3)$$

In addition, the equation (1) may be modified into the following equation (4).

$$\Delta A = \ln(I_b/I_a) = \ln(1+(I_b-I_a)/I_a) \quad (4)$$

Typically, since the relation of $\ln(I_b/I_a) \approx (I_b-I_a)/I_a$ is established from the relation of $(I_b-I_a) \ll I_a$, the equation (1) may be replaced with the following equation (5) as the variation $\Delta A$ of amount of light absorbed.

$$\Delta A \approx (I_b-I_a)/I_a \quad (5)$$

Hereinafter, when the light emitting element 1 emitting IR light and the light emitting element 1 emitting red light are required to be distinguished from each other, the light emitting element 1 emitting IR light will be referred to as a "light emitting element LD1" and the light emitting element 1 emitting red light will be referred to as a "light emitting element LD2." In addition, as one example, the light emitting element LD1 is assumed as the light emitting element 1 used for calculation of the blood flow and the light emitting elements LD1 and LD2 are assumed as light emitting elements 1 used for calculation of the oxygen saturation in the blood.

As described above, in the measurement of the blood flow, since the frequency difference $\Delta \omega_0$ of the beat signal observed in the light receiving element 3 falls within a frequency range having the upper limit of about several tens kHz, there may be used a method of flickering the light emitting element LD1 with a frequency which is at least twice as high as the frequency difference $\Delta \omega_0$ and acquiring the reflected light by the light emitting element LD1 in the light receiving element 3 for every emission interval during which the IR light is emitted from the light emitting element LD1.

At this time, in many cases, since important living-body information related to the blood flow is contained in a higher frequency region of the spectrum distribution with respect to the change in the amount of received light illustrated in FIG. 5, it is preferable to set a sampling period of the amount of received light in the light receiving element 3 to be as short as possible. To this end, the number of times of flickering per unit time of the light emitting element LD1 may be increased and the amount of received light of the light emitting element LD1, which is reflected at the living body 8, may be received in the light receiving element 3 in accordance with the emission interval of the light emitting element LD1.

However, in reality, there exist a time lag taken until a voltage applied to the light emitting element LD1 reaches a voltage required for emission and a time lag taken until the applied voltage reaches 0V after the applied voltage is stopped. Therefore, a waveform of the voltage applied to the light emitting element LD1 is not a square wave, but tends to be smoothly changed, for example, as illustrated in FIG. 8.

Figure 8:
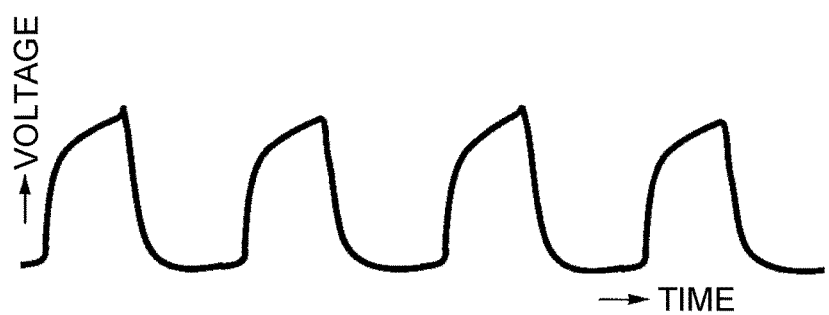
FIG. 8 is a view illustrating one example of a waveform of an applied voltage of a light emitting element.

In this way, the performance of an electronic device indicating regarding how to follow to an on/off of an applied voltage with an amount of time lag is referred to as "response performance." For an electronic device (in this example, the light emitting element LD1) with higher response performance, the waveform illustrated in FIG. 8 approaches a square wave and a variation of the applied voltage is converged into a predetermined range in the upper side of the square wave, so that the IR light with the stable amount of light may be emitted.

In the meantime, for an electronic device (in this example, the light emitting element LD1) with lower response performance, a waveform associated with the on/off of the applied voltage is likely to be distorted, which makes it difficult to irradiate the living body 8 with the IR light with the stable amount of light. Therefore, it is difficult to acquire a correct amount of received light from the light emitting element LD1 in the light receiving element 3, which may result in low accuracy of measurement of the blood flow.

In addition, while an effect of the response performance of an electronic device (e.g., the light emitting element LD1) on the measurement accuracy of the blood flow has been described above, there may be a case where low response performance of an electronic device such as the light receiving element 3 or other electronic devices deteriorates the measurement accuracy of the blood flow, similar to the case with the light emitting element LD1.

Therefore, even with an attempt to increase the number of times of flickering per unit time of the light emitting element LD1, there are restrictions on the response performance of an electronic device such as the light emitting element LD1, which often makes it difficult to precisely measure the living-body information.

In addition, when the oxygen saturation in the blood is measured, since it is known that the measurement frequency of the amount of received light is sufficient to fall within a range of about 30 Hz to about 1,000 Hz, the emission frequency of the light emitting element LD2, which indicates the number of times of flickering per one second of the light emitting element LD2, is also sufficient to fall within a range of about 30 Hz to about 1,000 Hz. That is, it is not necessary to adjust the emission frequency of the light emitting element LD2 to the emission frequency of the light emitting element LD1 by setting the emission frequency of the light emitting element LD2 to be lower than the emission frequency of the light emitting element LD1, so that the light emitting element LD1 and the light emitting element LD2 to emit light alternately. Therefore, the measurement accuracy of the oxygen saturation in the blood is less affected by the response performance of the light emitting element LD1 than the measurement accuracy of the blood flow.

Hereinafter, a living-body information measurement device for measuring plural living-body information with higher accuracy than a case where the light emitting element LD1 and the light emitting element LD2 emit light in an alternating manner will be described.

Figure 9:
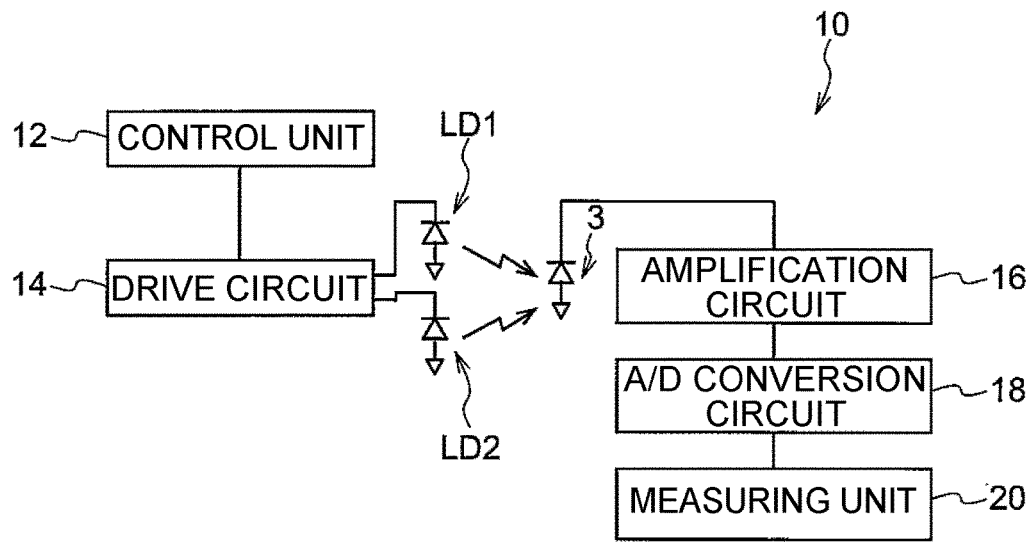
FIG. 9 is a view illustrating the configuration of a living-body information measurement device.

FIG. 9 is a view illustrating the configuration of a living-body information measurement device 10 according to an exemplary embodiment.

As illustrated in FIG. 9, the living-body information measurement device 10 includes a control unit 12, a drive circuit 14, an amplification circuit 16, an analog/digital (A/D) conversion circuit 18, a measuring unit 20, a light emitting element LD1, alight emitting element LD2, and alight receiving element 3.

The control unit 12 outputs a control signal, which controls a light-emission period and emission interval of each of the light emitting elements LD1 and LD2, to the drive circuit 14 including a power supply circuit for supplying drive power to the light emitting elements LD1 and LD2.

Upon receiving the control signal from the control unit 12, according to the light-emission period and emission interval instructed by the control signal, the drive circuit 14 supplies the drive power to the light emitting elements LD1 and LD2 so as to drive the light emitting elements LD1 and LD2.

The amplification circuit 16 amplifies a voltage corresponding to the intensity of light received in the light receiving element 3 up to a voltage level specified as an input voltage range of the A/D conversion circuit 18. In this example, the light receiving element 3 outputs a voltage corresponding to the intensity of received light. However, as another example, the light receiving element 3 may output a current corresponding to the intensity of received light. In this case, the amplification circuit 16 amplifies the current output by the light receiving element 3 up to a current level specified as an input current range of the A/D conversion circuit 18.

The A/D conversion circuit 18 receives the voltage amplified by the amplification circuit 16 as an input and digitizes the amount of light received in the light receiving element 3 which is expressed as the magnitude of the voltage.

The measuring unit 20 receives the amount of received light digitized by the A/D conversion circuit 18 as an input, calculates a spectrum distribution for each frequency $\omega$ by subjecting the amount of received light emitted by the light emitting element LD1 to the FFT, and measures a blood flow by integrating the product of the frequency $\omega$ and the power spectrum at the frequency $\omega$ with respect to the frequency $\omega$.

In addition, the measuring unit 20 receives the amount of received light digitized by the A/D conversion circuit 18 as an input and manages the amount of received light emitted by the light emitting element LD1 and the light emitting element LD2 in a chronological order. Then, the measuring unit 20 measures an oxygen saturation by calculating a variation $\Delta A_{IR}$ of amount of light absorbed of the light emitting element LD1 and a variation $\Delta A_{Red}$ of amount of light absorbed of the light emitting element LD2 according to the equation (1) and calculating a ratio of amount of light absorbed variation $\Delta A_{Red}$ to amount of light absorbed variation $\Delta A_{IR}$ according to the equation (2).

Figure 10:
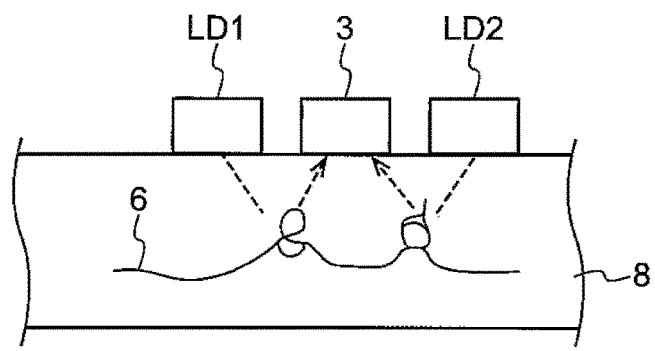
FIG. 10 is a view illustrating one example of an arrangement of a light emitting element and a light receiving element.

FIG. 10 illustrates one example of arrangement of the light emitting elements LD1 and LD2 and the light receiving element 3 in the living-body information measurement device 10. As illustrated in FIG. 10, the light emitting elements LD1 and LD2 and the light receiving element 3 are arranged side by side with facing one surface of the living body 8. In this example, the light receiving element 3 receives light of the light emitting elements LD1 and LD2 which is reflected at the living body 8.

Figure 11:
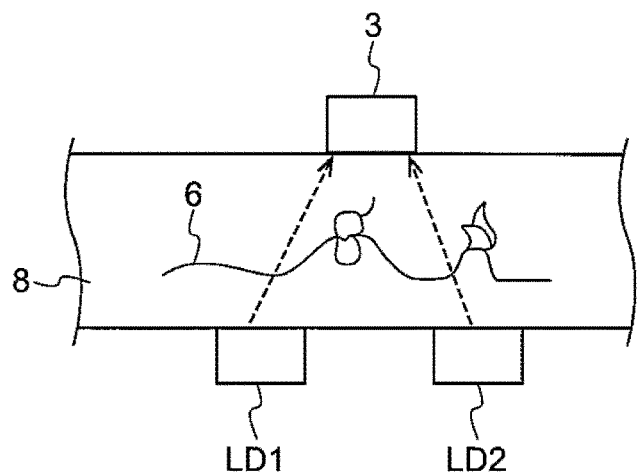
FIG. 11 is a view illustrating another example of an arrangement of a light emitting element and a light receiving element.

However, the arrangement of the light emitting elements LD1 and LD2 and the light receiving element 3 is not limited to the arrangement example of FIG. 10. For example, as illustrated in FIG. 11, the light emitting elements LD1 and LD2 may be arranged to face the light receiving element 3 with the living body 8 sandwiched therebetween. In this example, the light receiving element 3 receives light of the light emitting elements LD1 and LD2 which transmits through the living body 8.

Although in these examples the light emitting elements LD1 and LD2 are both vertical cavity surface-emission lasers, the light emitting elements LD1 and LD2 are not limited thereto but may be edge-emission lasers.

When a blood flow is to be measured by the measuring unit 20, since this measurement is made based on a spectrum distribution of the amount of received light according to a beat signal as described above, a laser device which may generate a beat signal more easily than different light may be preferably used for the light emitting element LD1.

However, even if the light emitted from the light emitting element LD2 is not a laser beam, since the amount of light absorbed variation $\Delta A_{Red}$ of the light emitting element LD2 may be calculated, a light emitting diode (LED) or an organic light emitting diode (OLED) may be used for the light emitting element LD2.

Next, the configuration of main parts of an electric system of the living-body information measurement device 10 according to this exemplary embodiment will be described with reference to FIG. 12.

Figure 12:
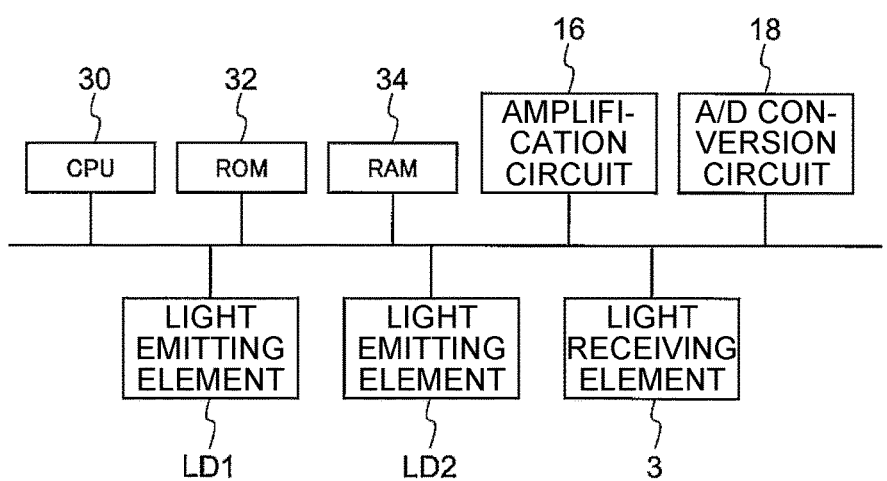
FIG. 12 is a view illustrating an exemplary configuration of main parts of an electric system of the living-body information measurement device.

As illustrated in FIG. 12, the living-body information measurement device 10 according to this exemplary embodiment includes a control part for controlling a light-emission period and an emission interval of each of the light emitting element LD1 and the light emitting device LD2, and a central processing unit (CPU) 30 as one example of a measuring unit for measuring a blood flow and an oxygen saturation in the blood in the living body 8. In addition, the living-body information measurement device 10 includes a read only memory (ROM) 32 in which a variety of programs and parameters are stored, and a random access memory (RAM) 34 used as a work area or the like when the variety of programs are executed by the CPU 30.

The CPU 30, the ROM 32 and the RAM 34 are connected to one another via an internal bus 36 of the living-body information measurement device 10. In addition, the light emitting element LD1, the light emitting element LD2, the light receiving element 3, the amplification circuit 16 and the A/D conversion circuit 18 are connected to the internal bus 36. In addition, a timer for measuring elapsed time from a specified point of time is contained in the CPU 30.

Next, an operation of the living-body information measurement device 10 will be described with reference to FIG. 13.

Figure 13:
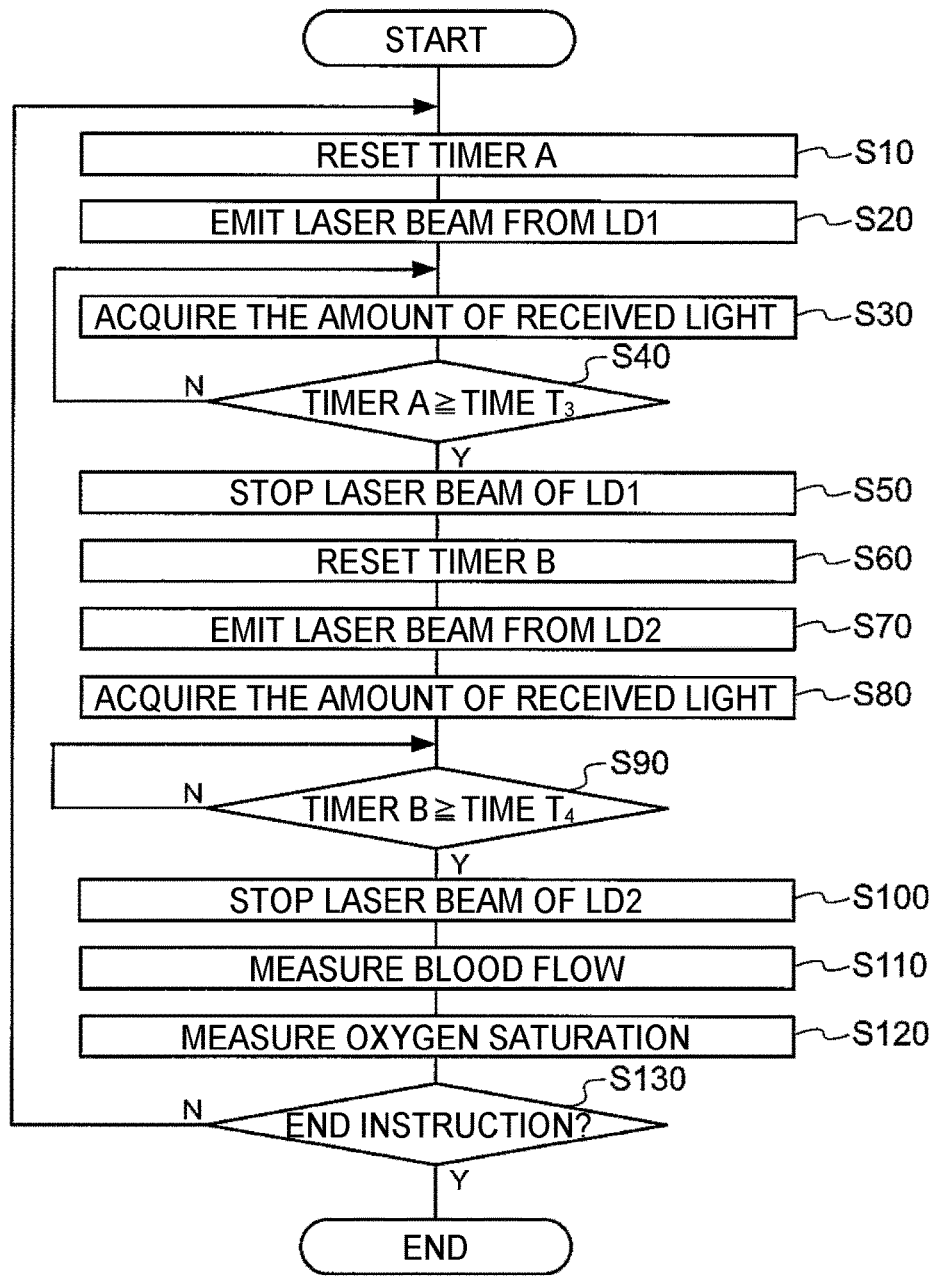
FIG. 13 is a flowchart illustrating one example of a flow of living-body information measuring process.

FIG. 13 is a flow chart illustrating one example of a flow of living-body information measuring process executed by the CPU 30 when the CPU 30 receives an instruction to start measurement of living-body information. A program defining the living-body information measuring process (a living-body information measurement program) is in advance installed in, e.g., the ROM 32. In addition, it is assumed that the light emitting element LD1 and the light emitting element LD2 are both in an emission stop state where no laser beam is emitted at a point of time of start of the living-body information measurement program.

First, at Step S10, the CPU 30 resets a timer A contained in the CPU 30. Here, "resetting a timer" means that measurement by the timer is stopped and the timer newly starts to count the elapsed time from the stop point of the timer.

At Step S20, the CPU 30 informs the drive circuit 14 of an emission start instruction to instruct an emission start of the light emitting element LD1. Upon receiving the emission start instruction, the drive circuit 14 supplies drive power to the light emitting element LD1 and causes the light emitting element LD1 to emit a laser beam.

At Step S30, the CPU 30 acquires the amount of light, which is emitted by the light emitting element LD1 and received in the light receiving element 3, from the A/D conversion circuit 18 and stores the acquired amount of light in a preset area of the RAM 34.

At Step S40, the CPU 30 determines whether or not the timer A is elapsing time $T_3$ or more after resetting the timer A at Step S10. The time $T_3$ is a parameter stored in a preset area of the ROM 32 and determines the length of the emission interval of the light emitting element LD1.

When a result of the determination at Step S40 is negative, the process proceeds to Step S30 to repeat the acquiring process of the amount of light, which is emitted by the light emitting element LD1 and received in the light receiving element 3, from the A/D conversion circuit 18. Then, the CPU 30 repeats Step S30 until the timer A has elapsed time $T_3$ or more. That is, the CPU 30 acquires the amount of received light by the light emitting element LD1 plural times in a state of continued emission of the light emitting element LD1 over time $T_3$ or more.

In the meantime, when the result of the determination at Step S40 is affirmative, the process proceeds to Step S50.

At Step S50, the CPU 30 informs the drive circuit 14 of an emission stop instruction to instruct an emission stop of the light emitting element LD1. Upon receiving the emission stop instruction, the drive circuit 14 stops the supply of drive power to the light emitting element LD1 and causes the light emitting element LD1 to stop the emission of the laser beam.

At Step S60, the CPU 30 resets a timer B contained in the CPU 30.

At Step S70, the CPU 30 informs the drive circuit 14 of an emission start instruction to instruct an emission start of the light emitting element LD2. Upon receiving the emission start instruction, the drive circuit 14 supplies drive power to the light emitting element LD2 and causes the light emitting element LD2 to emit a laser beam.

At Step S80, the CPU 30 acquires the amount of light, which is emitted by the light emitting element LD2 and received in the light receiving element 3, from the A/D conversion circuit 18 and stores the acquired amount of light in a preset area of the RAM 34.

At Step S90, the CPU 30 determines whether or not the timer B is elapsing time $T_4$ or more after resetting the timer B at Step S60. The time $T_4$ is a parameter stored in a preset area of the ROM 32 and determines the length of the emission interval of the light emitting element LD2.

In addition, as described above, since the measurement period of the amount of received light of the light emitting element LD2 required to measure the oxygen saturation in blood may be shorter than the measurement period of the amount of received light of the light emitting element LD1 required to measure the blood flow, it is preferable to set time $T_4$ to be smaller than time $T_3$ and set the emission interval of the light emitting element LD2 to be shorter than the emission interval of the light emitting element LD1. By setting Time $T_4$ in this way, it is possible to increase the number of times of measurement of the oxygen saturation in blood in unit time without deteriorating the measurement accuracy of the oxygen saturation in blood, as compared to a case where time $T_4$ is set to be larger than time $T_3$.

When a result of the determination at Step S90 is negative, the CPU 30 repeats Step S90 and stands by until the timer B has elapsed time $T_4$ or more. In the meantime, when the result of the determination at Step S90 is affirmative, the process proceeds to Step S100.

At Step S100, the CPU 30 informs the drive circuit 14 of an emission stop instruction to instruct an emission stop of the light emitting element LD2. Upon receiving the emission stop instruction, the drive circuit 14 stops the supply of drive power to the light emitting element LD2 and causes the light emitting element LD2 to stop the emission of the laser beam.

At Step S110, according to the above-described blood flow measuring method, the CPU 30 calculates a spectrum distribution for each frequency ω by subjecting time series data of the amount of received light of the light emitting element LD1 acquired at Step S30 to the FFT, and measures a blood flow by integrating the calculated spectrum distribution with respect to the entire frequency ω.

At Step S120, according to the above-described blood oxygen saturation measuring method, the CPU 30 stores a pair of the amount of received light of the light emitting element LD1 lastly acquired at Step S30 and the amount of received light of the light emitting element LD2 acquired at Step S80 in a preset area of the RAM 34. Then, the CPU 30 measures the oxygen saturation in the blood by using the time series data of the pair of the amount of received light to calculate the equations (1) and (2) or known equations obtained by modifying these equations (1) and (2).

At Step S130, the CPU 30 determines whether or not an end instruction is received to end the measurement of living-body information. When a result of the determination at Step S130 is negative, the process returns to Step S10 and the CPU 30 continues to measure the blood flow and the oxygen saturation in the blood by repeating Steps S10 to S130 until the end instruction is received.

Figure 14:
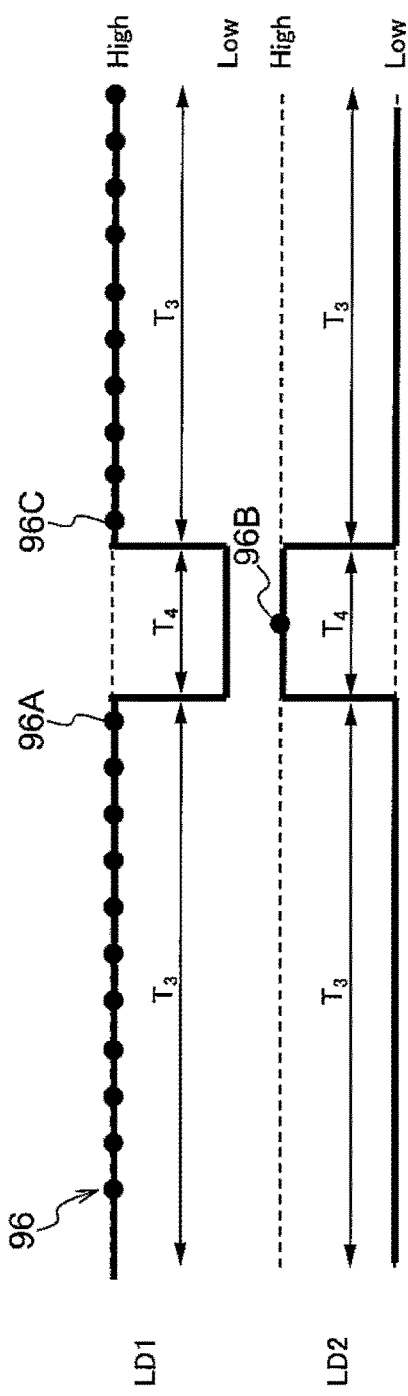
FIG. 14 is a timing chart illustrating one example of an emission timing of a light emitting element emitting IR light and a light emitting element emitting red light, and a light receiving timing of a light receiving element.

FIG. 14 is a timing chart illustrating one example of emission timings of the light emitting elements LD1 and LD2 when the living-body information measurement program of FIG. 13 is executed.

As illustrated in FIG. 14, a light-emission period having the length of time $T_3$ and an emission stop period having the length of time $T_4$ repeatedly appear in the light emitting element LD1. Conversely, an emission stop period having the length of time $T_3$ and a light-emission period having the length of time $T_4$ repeatedly appear in the light emitting element LD2.

In addition, according to Steps S30 and S40 of FIG. 13, the living-body information measurement device 10 acquires the amount of received light of the light emitting element LD1 at plural light receiving points 96 while continuously emitting the laser beam from the light emitting element LD1.

Figure 15:
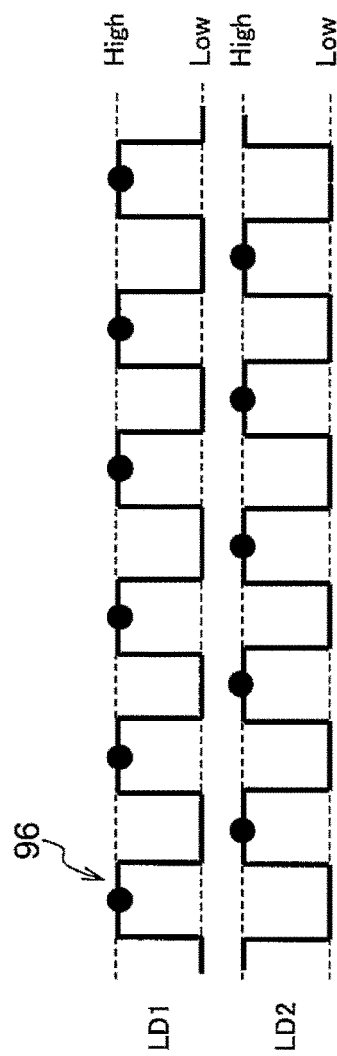
FIG. 15 is a timing chart illustrating one example of a light receiving timing when a light emitting element emitting IR light and a light emitting element emitting red light are alternately flickered.

Therefore, in measuring the blood flow, as illustrated in FIG. 15, by increasing the number of times of flickering per unit time of the light emitting element LD1 and acquiring the amount of received light of the light emitting element LD1 at one light receiving point 96 located for each light-emission period of the light emitting element LD1, the measurement accuracy of the blood flow is less affected by the response performance of the light emitting element LD1 associated with the flickering of the light emitting element LD1, as compared to a case where the sampling period of the amount of received light of the light emitting element LD1 is short. That is, by increasing the number of times of flickering per unit time of the light emitting element LD1, as compared to a case where the sampling period of the amount of received light reflected of the light emitting element LD1 is shortened, the living-body information measurement device 10 may shorten the sampling period of the amount of received light of the light emitting element LD1.

As used herein, the phrase "while continuously emitting the laser beam from the light emitting element LD1" is not limited to a state of emitting the laser beam from the light emitting element LD1 over the entire light-emission period of the light emitting element LD1 as described above. For example, this may include a state of emitting the laser beam from the light emitting element LD1 in accordance with the sampling period of the amount of received light of the light emitting element LD1, once stopping the emission of the laser beam from the light emitting element LD1 within a range in which the quantity of the laser beam of the light emitting element LD1 at each light receiving point 96 is unaffected by the response performance of the light emitting element LD1 associated with the on/off control of the light emitting element LD1, and then restarting the emission of the laser beam.

In addition, the measuring unit 20 of the living-body information measurement device 10 measures the oxygen saturation in the blood by using the amount of received light of the light emitting element LD2 acquired at a light receiving point 96B among the light receiving points 96 indicating acquisition timings of the amount of received light of the light emitting elements LD1 and LD2, and the amount of received light of the light emitting element LD1 acquired at one light receiving point 96 during the light-emission period of the light emitting element LD1 adjacent along a time axis to the light-emission period of the light emitting element LD2 including the light receiving point 96B. In this case, it is preferable to combine the amount of received light of the light emitting element LD1 at a light receiving point 96A or a light receiving point 96C adjacent to the light receiving point 96B with the amount of received light of the light emitting element LD2 at the light receiving point 96B.

This is because the use of the amount of received light of the light emitting element LD1 and the amount of received light of the light emitting element LD2 which are as temporarily close to each other as possible tends to increase the measurement accuracy of the oxygen saturation in the blood.

Although the example of once acquiring the amount of received light of the light emitting element LD2 in the light-emission period of the light emitting element LD2 is shown in the flow chart of the living-body information measurement program illustrated in FIG. 13, the amount of received light of the light emitting element LD2 may be acquired plural times.

Figure 16:
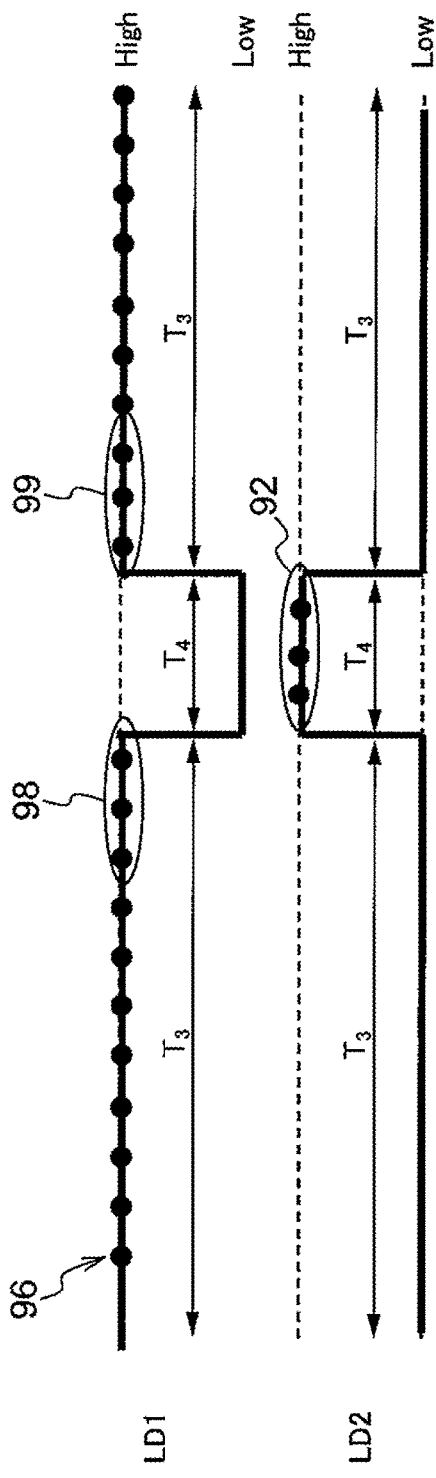
FIG. 16 is a timing chart illustrating another example of an emission timing of a light emitting element emitting IR light and a light emitting element emitting red light, and a light receiving timing of a light receiving element.

FIG. 16 is a timing chart illustrating one example of acquiring the amount of received light of the light emitting element LD2 in the light-emission period of the light emitting element LD2 plural times. In the example of FIG. 16, the amount of received light of the light emitting element LD2 is acquired three times in a light-emission period of the light emitting element LD2 indicated by a region 92. It is to be understood that the number of times of acquisition of the amount of received light of the light emitting element LD2 is not limited to three but may be two or more.

In this case, the measuring unit 20 assumes an average of the amounts of received light acquired at the light receiving points 96 in the light-emission period of the light emitting element LD2 indicated by the region 92 as the amount of received light in the light-emission period of the light emitting element LD2 indicated by the region 92. In addition, the measuring unit 20 assumes a average of the amounts of received light acquired at the light receiving points 96 in a light-emission period of the light emitting element LD1 adjacent to the light-emission period of the light emitting element LD2 as the amount of received light in the light-emission period of the light emitting element LD1. Then, the measuring unit 20 calculates the oxygen saturation in the blood based on a combination of the amount of received light in the light-emission period of the light emitting element LD1 and the amount of received light in the light-emission period of the light emitting element LD2.

A way of selecting plural light receiving points 96 in the light-emission period of the light emitting element LD1 is not particularly limited. However, it is preferable to select the light receiving points 96 which are adjacent to the light receiving points 96 in the light-emission period of the light emitting element LD2 indicated by the region 92 as much as possible. For example, the same number of adjacent light receiving points 96 as the light receiving points 96 included in the region 92 may be selected. Alternatively, the light receiving points 96 included in a region 98 or a region 99 may be selected. As described above, this is because the use of the amount of received light of the light emitting element LD1 and the amount of received light of the light emitting element LD2 which are as temporarily close to each other as possible tends to increase the accuracy of measurement of the oxygen saturation in blood.

Figure 17:
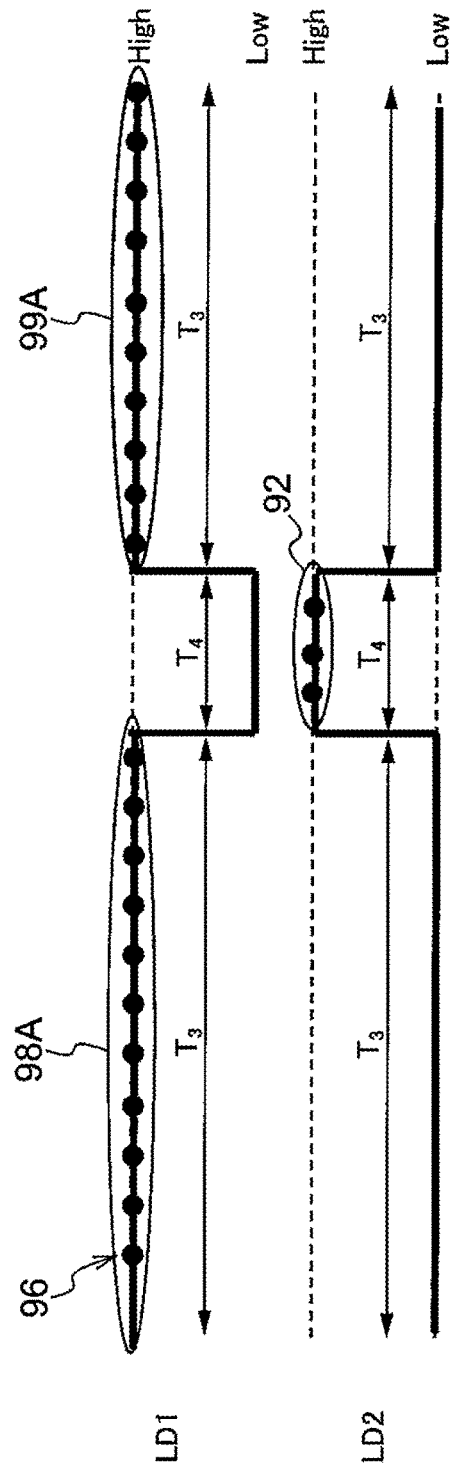
FIG. 17 is a timing chart illustrating another example of an emission timing of a light emitting element emitting IR light and a light emitting element emitting red light, and a light receiving timing of a light receiving element.

In addition, there is no limitation in the number of light receiving points 96 selected in the light-emission period of the light emitting element LD1 to be used to calculate the oxygen saturation in the blood. In the example of FIG. 16, the same number of adjacent light receiving points 96 as the light receiving points 96 in the light-emission period of the light emitting element LD2 indicated by the region 92 is selected. However, for example, as indicated by a region 98A or a region 99A in FIG. 17, all light receiving points 96 included in one light-emission period of the light emitting element LD1 may be selected. With the increase in the number of selected light receiving points 96 of the light emitting element LD1, frequency differences $\Delta\omega_0$ of beat signals included in the IR light received from the light emitting element LD1 are averaged and the calculation of the oxygen saturation in the blood is less affected by the beat signals acting as noise components.

In this way, with the living-body information measurement device 10 according to the exemplary embodiment, it is possible to acquire the amount of received light of the light emitting element LD1 at plural light receiving points 96 while emitting the laser beam from the light emitting element LD1.

As a result, by increasing the number of times of flickering of the light emitting element LD1 per unit time, as compared to a case where the sampling period of the amount of received light reflected at the living body 8 is shortened, the sampling period of the amount of received light may be shortened, thereby allowing the living-body information to be measured with a higher accuracy.

In addition, the living-body information measurement device 10 may be used for measurement of other living-body information without being limited to the above-mentioned living-body information.

In addition, the living-body information measurement device 10 may be used for measurement of the blood velocity as well as the blood flow, as described above. In addition, as illustrated in FIG. 7, since the amount of light received in the light receiving element 3 varies depending on the pulse of arteries 4, it is possible to measure a pulse rate from the variation of the amount of light received in the light receiving element 3. In addition, it is possible to measure an acceleration pulse wave by twice differentiating a waveform obtained by measuring a change in pulse rate in a chronological order. The acceleration pulse wave is used for estimation of blood vessel age, diagnosis of arteriosclerosis, or the like.

In addition, the living-body information measurement device 10 may be used for measurement of other living-body information without being limited to the above-mentioned living-body information.

In addition, although it has been illustrated in the exemplary embodiments that the processes in the control unit 12 and the measuring unit 20 are implemented with software, a process similar to the flow chart illustrated in FIG. 13 may be implemented with hardware. In this case, the processes in the control unit 12 and the measuring unit 20 may be performed more quickly than those implemented with software.

Furthermore, although it has been illustrated in the exemplary embodiments that the living-body information measurement program is installed in the ROM 32, the exemplary embodiments are not limited thereto. The living-body information measurement program according to the exemplary embodiments may be provided in the form of a computer-readable recording medium recording the program. For example, the living-body information measurement program according to the exemplary embodiments may be provided in the form of a portable recording medium recording the program, such as a compact disc (CD)-ROM, a digital versatile disc (DVD)-ROM, a universal serial bus (USB) memory or the like. Furthermore, the living-body information measurement program according to the exemplary embodiments may be provided in the form of a semiconductor memory recording the program, such as a flash memory or the like.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A living-body information measurement device comprising:
   a first light emitting element configured to emit a first wavelength of light;
   a second light emitting element configured to emit a second wavelength of light shorter than the first wavelength; and
   at least one hardware processor configured to implement:
      controlling the first light emitting element to emit the first wavelength of light;
      controlling the second light emitting element to emit the second wavelength of light;
      controlling a light receiving element that receives the light emitted from the first light emitting element and the second light emitting element;
      controlling a continuous light-emission period of each of the first light emitting element and the second light emitting element so that the continuous light-emission period of the second light emitting element is shorter than the continuous light-emission period of the first light emitting element; and
      controlling a measurement of a plurality of living-body information based on the light received in the light receiving element; and
   determining an oxygen saturation according to the light emitted from the first and second light emitting elements as one of plurality of the living-body information,
   wherein light emitted from the first light emitting element is a laser beam.

2. The living-body information measurement device according to claim 1,
   wherein the measurement comprises measuring the plurality of living-body information by using an amount of light, which is emitted by the first light emitting element and received in the light receiving element over a plurality of times, for every light-emission period of the first light emitting element, and an amount of received light in a light-emission period of the second light emitting element adjacent to the light-emission period of the first light emitting element.

3. The living-body information measurement device according to claim 1,
   wherein controlling the continuous light-emission period of each of the first light emitting element and the second light emitting element comprises controlling the light-emission periods of the first light emitting element and the second light emitting element so that the light-emission periods do not overlap with each other.

4. The living-body information measurement device according to claim 1,
   wherein the measurement comprises measuring the plurality of living-body information based on a frequency spectrum for an amount of light emitted by the first light emitting element and received in the light receiving element, the amount of light emitted by the first light emitting element and received in the light receiving element, and an amount of light emitted by the second light emitting element and received in the light receiving element.

5. The living-body information measurement device according to claim 1,
   wherein the measurement comprises acquiring an amount of received light from the light receiving element over a plurality of times in at least one of the light-emission period of the first light emitting element and the light-emission period of the second light emitting element, and assuming an average of the acquired amounts of received light as an amount of received light during a light-emission period when the amount of the received light is acquired from the light receiving element over the plurality of times.

6. The living-body information measurement device according to claim 1,
   wherein the measurement comprises measuring another living-body information including at least one of a blood flow, a blood velocity and a blood volume, as the plurality of living-body information.

7. The living-body information measurement device according to claim 1,
   wherein the first wavelength is a wavelength of infrared light, and
   wherein the second wavelength is a wavelength of red light.

8. The living-body information measurement device according to claim 7,
wherein the living-body information comprises at least a blood flow and an oxygen saturation,
wherein the at least one hardware processor is further configured to implement:
determining the blood flow according to first signals obtained from first emissions of the infrared light at the first wavelength; and
determining the oxygen saturation according to second signals obtained from a combination of the first emissions of the infrared light at the first wavelength and also second emissions of the red light at the second wavelength.

9. The living-body information measurement device according to claim 8,
wherein the continuous light-emission period of the second light emitting element is less than half of the continuous light-emission period of the first light emitting element,
wherein the at least one hardware processor is further configured to perform a selection of:
a first number of first samples from the first signals;
a second number of second samples from the second signals, the second number being at most half of the first number, and
wherein the at least one hardware processor is further configured to determine the oxygen saturation according to the selection.

10. The living-body information measurement device according to claim 9, wherein at least a plurality of the first samples are excluded from the selection.

11. The living-body measurement device according to claim 8, wherein the infrared light is the laser beam.

12. The living-body information measurement device according to claim 1,
wherein the at least one hardware processor is further configured to implement:
determining at least one of a blood flow, a blood velocity and a blood volume according to the light emitted form the first light emitting element as the plurality of living-body information.

13. A non-transitory computer readable medium storing a living-body information measurement program that, when executed, causes a computer to implement:
controlling a first light emitting element, configured to emit a first wavelength of light, and a second light emitting element configured to emit a second wavelength of light shorter than the first wavelength;
controlling a light receiving element that receives the light emitted from the first light emitting element and the second light emitting element;
controlling a continuous light-emission period of each of the first light emitting element and the second light emitting element so that the continuous light-emission period of the second light emitting element is shorter than the continuous light-emission period of the first light emitting element;
measuring a plurality of living-body information based on the light received in the light receiving element; and
determining an oxygen saturation according to the light emitted from the first and second light emitting elements as one of the living-body information,
wherein the light emitted from the first light emitting element is a laser beam.

14. A living-body information measurement device comprising:
a first light emitting element configured to emit a first wavelength of light;
a second light emitting element configured to emit a second wavelength of light shorter than the first wavelength; and
at least one hardware processor configured to implement:
controlling the first light emitting element to emit the first wavelength of light;
controlling the second light emitting element to emit the second wavelength of light;
controlling a light receiving element that receives the light emitted from the first light emitting element and the second light emitting element;
controlling a continuous light-emission period of each of the first light emitting element and the second light emitting element so that the continuous light-emission period of the second light emitting element is shorter than the continuous light-emission period of the first light emitting element; and
controlling a measurement of a plurality of living-body information based on the light received in the light receiving element,
wherein the first wavelength is a wavelength of infrared light,
wherein the second wavelength is a wavelength of red light,
wherein the living-body information comprises at least a blood flow and an oxygen saturation,
wherein the at least one hardware processor is further configured to implement:
determining the blood flow according to first signals obtained from first emissions of the infrared light at the first wavelength;
determining the oxygen saturation according to second signals obtained from a combination of the first emissions of the infrared light at the first wavelength and also second emissions of the red light at the second wavelength,
wherein the continuous light-emission period of the second light emitting element is less than half of the continuous light-emission period of the first light emitting element,
wherein the at least one hardware processor is further configured to perform a selection of:
a first number of first samples from the first signals;
a second number of second samples from the second signals, the second number being at most half of the first number, and
wherein the at least one hardware processor is further configured to determine the oxygen saturation according to the selection.

* * * * *